United States Patent [19]
Ohsato et al.

[11] 3,983,527
[45] Sept. 28, 1976

[54] HUMIDITY-SENSITIVE SENSOR

[75] Inventors: Nobuyoshi Ohsato, Itami; Kenzo Sono, Nishinomiya; Keihachiro Tanaka, Itami, all of Japan

[73] Assignee: Nippon Sheet Glass Co., Ltd., Osaka, Japan

[22] Filed: Aug. 12, 1974

[21] Appl. No.: 496,856

[30] Foreign Application Priority Data

| Aug. 14, 1973 | Japan | 48-91449 |
| Nov. 6, 1973 | Japan | 48-124008 |
| Dec. 26, 1973 | Japan | 49-1934 |
| Jan. 7, 1974 | Japan | 49-5525 |
| Mar. 25, 1974 | Japan | 49-33697 |
| Mar. 8, 1974 | Japan | 49-27666[U] |
| Apr. 26, 1974 | Japan | 49-48854[U] |

[52] U.S. Cl. ................. 338/35; 73/336.5; 200/61.04; 219/203; 219/522; 427/126; 428/328; 428/329
[51] Int. Cl.² ......................... H01C 13/00
[58] Field of Search ......... 338/35, 34, 308; 200/61.04; 73/336.5; 23/254 E, 255 E; 340/235; 219/203, 522; 427/123, 125, 126; 428/328, 329, 402, 403

[56] References Cited
UNITED STATES PATENTS

| 2,937,524 | 5/1960 | Gregor | 338/35 X |
| 3,671,913 | 6/1972 | Mamiya et al. | 338/35 |
| 3,686,606 | 8/1972 | Thoma | 338/35 |
| 3,848,218 | 11/1974 | Wakabayashi | 338/35 |
| 3,868,492 | 2/1975 | Taylor | 338/35 X |

*Primary Examiner*—C. L. Albritton
*Attorney, Agent, or Firm*—Wenderoth, Lind & Ponack

[57] ABSTRACT

A humidity-sensitive sensor, especially useful on the window of an automobile with the sensor on the inside surface of the glass. The sensor has a pair of spaced electrodes and a humidity-sensitive coating composed of a hydroscopic resin extending over the pair of electrodes. The resin can be an acrylate resin or a methacrylate resin, and preferably is a resin which has a volume change of at least 10% in response to a 50% change in humidity. Dispersed in the resin are electrically conductive particles, preferably in an amount of from 20 to 60% by volume of the amount of resin. The sensor, prior to its use in an operating device, is preferably exposed to a high humidity condition and a low humidity condition at least thirty times in order to stabilize it.

11 Claims, 15 Drawing Figures

HUMIDITY-SENSITIVE SENSOR

This invention relates to a humidity-sensitive sensor, and more specifically to a humidity-sensitive sensor the electric resistance of which changes according to changes in humidity.

In recent years, humidity-sensitive sensors for detecting the humidity and automatically controlling various apparatuses according to changes in humidity have been used in a number of apparatuses including automatic water droplet removing devices for the prevention of dew formation in the rear window glass of automobiles, air-conditioners in buildings, refrigerators, food drying devices, weather condition measuring instruments or precision instruments. For example, in an automatic water droplet removing apparatus in which electric current flows in a resistance element formed of an electrically conducting material such as a noble metal coating, conducting metallic oxide coating or fine metallic wire bonded to windowglass to elevate the temperature of the glass thereby to evaporate moisture which has been adsorbed at the surface of the glass, a humidity-sensitive sensor for detecting the presence of water droplets on the surface of the glass and controlling the supply of electric current to the resistance element is used. This humidity-sensitive sensor is made of a pair of facing electrodes spaced from each other on the surface of the glass and a predetermined electric potential is applied thereto. According to the humidity between the electrodes, the space between them becomes electrically conductive or non-conductive, whereby the humidity on the surface of glass is detected, and thus, the supply of electric current to the resistance element is controlled. When moisture in the air adheres to the surface of glass and water droplets or a water phase is formed in the space between the electrodes, electric current flows between the electrodes. By utilizing this electric current, a control circuit for controlling the current supply to the resistance element is actuated to supply current automatically to the resistance element and thus heat the glass and evaporate the water droplets. When the water droplets have been evaporated by the heating of glass and the space between the electrodes becomes electrically non-conductive, the supply of current to the resistance element stops automatically.

The conventional humidity-sensitive sensor as described above however has the defect that an alternating current must be used as a source of electric potential for the electrodes. It is known that when a direct current source is used, the resistance between the electrodes via the moisture condensed to dew becomes gradually higher, and the sensor finally fails to function properly. It is thought that the carrier for electric current flowing between the electrodes is the sodium ions in the glass composition which have dissolved out onto the surface of the glass when the moisture adheres to the space between the electrodes, and that the sodium ions moves gradually to the cathode when the direct current flows, whereby the concentration of the carrier increases in the vicinity of the cathode but decreases in the vicinity of the anode (so-called polarization occurs), and thus, the resistance increases. Accordingly, in order to avoid this polarization phenomenon, it is necessary to use an alternating current with a very small proportion of a direct current component.

Furthermore, in the conventional humidity-sensitive sensor, the absolute value of the resistance between the electrodes is exceedingly high because of the small absolute amount of the carrier in the conductive state, and it is difficult to cause current to flow between the electrodes in a sufficiently large amount because changes in resistance value according to changes in the amount of moisture are small. Moreover, it is difficult to increase the sensitivity (changes in current according to fluctuations in the amount of moisture) to a sufficient degree. Accordingly, the gain of the control circuit must be enlarged, and the control circuit becomes expensive.

Accordingly, a main object of this invention is to provide a humidity-sensitive sensor which can permit the use of both alternating and direct currents.

Another object of this invention is to provide a humidity-sensitive sensor of the above type having good sensitivity.

Another object of this invention is to provide a humidity-sensitive sensor of the above type having a long life.

Still another object of this invention is to provide a humidity sensor suitable especially for an automatic water droplet removing device for windowpanes of automobiles.

A further object of this invention is to provide a method for producing a humidity-sensitive sensor of the above type with simplicity and at low cost.

According to this invention, there is provided a humidity-sensitive sensor comprising a pair of spaced electrodes and a humidity-sensitive coating composed of a hygroscopic resin having electrically conductive particles dispersed therein and extending between said pair of electrodes.

In the humidity-sensitive sensor of this invention, the resistance between the two electrodes changes according to changes in the humidity of the atmosphere. Conduction of electric current between the electrodes is performed by the electrically conductive particles dispersed in the hygroscopic resin. When the humidity of the atmosphere becomes high, the hygrocopic resin undergoes volumetric expansion to increase distances between the electrically conductive particles and thus increase the electric resistance between the two electrodes. If the humidity of the atmosphere becomes low, the hygroscopic resin shrinks and the distances between the electrically conducting particles decrease or the particles contact each other, resulting in a decrease in electric resistance between the electrodes.

The above and other objects of this invention along with its advantages will become apparent from the following description taken in conjunction with the accompanying drawings in which.

Referring to the accompanying drawings, preferred embodiments of the humidity-sensitive sensor in accordance with the present invention will be described mainly in connection with an automatic water droplet removing apparatus for windowglass of automobiles. However, the humidity-sensitive sensor in accordance with this invention is not limited to the application to the automatic water droplet removing apparatus, but can be applied equally to a number of devices where changes in humidity are desired to be converted to changes of electric resistance.

Figure 1:
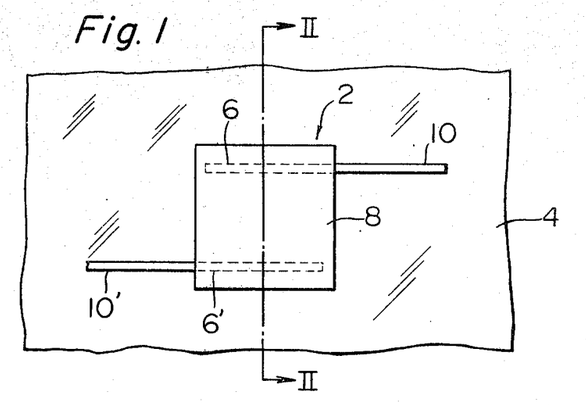
FIG. 1 is a plan view of one embodiment of the humidity-sensitive sensor in accordance with this invention.
Figure 2:
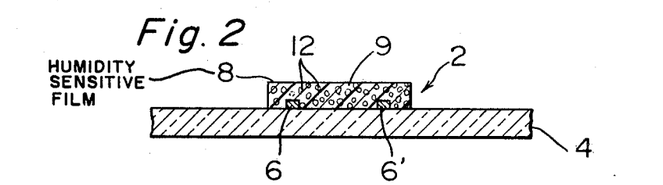
FIG. 2 is a sectional view taken along the line II—II of FIG. 1.

Referring to FIGS. 1 and 2, a humidity-sensitive sensor according to this invention shown generally at 2 consists of a pair of metal electrodes 6 and 6' which are spaced from each other and are fixed for example by baking on a non-conductive base plate such as a window glass of an automobile, and a humidity-sensitive film coated so as to cover the pair of electrodes 6 and 6' and cured. The electrodes 6 and 6' include lead portions 10 and 10' respectively which extend outwardly from the humidity-sensitive film.

The humidity-sensitive film 8 consists of a hygroscopic resin 9 the volume of which changes according to changes in humidity, preferably expands or shrinks at least 10% in response to 50% change in humidity in an atmosphere having a relative humidity of at least 40%, and a number of electrically conductive particles 12 dispersed in the hygroscopic resin 9. When the relative humidity of the atmosphere increases, the volume of the hygroscopic resin 9 in this humidity-sensitive film 8 expands, and the distances between the electrically conductive particles dispersed in it become relatively large, which in turn results in an increased electric resistance between the electrodes 6 and 6'. Conversely, when the relative humidity of the atmosphere decreases, the hygroscopic resin 9 shrinks, and the distances between the electrically conductive particles 12 dispersed in it become very small or they contact each other, in which case the electric resistance between the electrodes 6 and 6' is reduced.

Examples of the hygroscopic resins the volume of which changes according to changes in the relative humidity of the atmosphere include acrylate polymers, methacrylate polymers, polyvinyl alcohol, polyvinyl acetals, polyacrylamides, polyvinyl pyrrolidone, polyethylene oxide, polyethyleneimine, hydroxyethyl cellulose, and cellophane. The acrylate and methacrylate polymers are especially preferred because of their high degrees of change in volume according to changes in relative humidity, high strength in the expanded state, and good reversibility between volumetric expansion and contraction.

The hygroscopic acrylate or methacrylate polymers may, for example, be hydroxy lower alkyl acrylates, hydroxy lower alkyl methacrylates, hydroxy lower alkoxy lower alkyl acrylates, or hydroxy lower alkoxy lower alkyl methacrylates, the hydroxy lower alkyl acrylates and methacrylates being especially preferred. Specific examples of these monomers are 2-hydroxyethyl acrylate, 2-hydroxyethyl methacrylate, diethylene glycol monoacrylate, diethylene glycol monomethacrylate, triethylene glycol monoacrylate, triethylene glycol monomethacrylate, 2-hydroxypropyl acrylate, 2-hydroxypropyl methacrylate, 3-hydroxypropyl acrylate, 3-hydroxypropyl methacrylate, dipropylene glycol monoacrylate, and dipropylene glycol monomethacrylate. The 2-hydroxyethyl methacrylate is especially preferred. If desired, the above polymers may contain copolymerized therewith such a comonomer as acrylic acid, methacrylic acid, itaconic acid, maleic acid, fumaric acid or mono-2-hydroxypropyl itaconate.

The polyvinyl alcohol may be not only a completely saponified product of polyvinyl acetate but also a partially saponified product thereof. Examples of polyvinyl acetal include polyvinyl formal, polyvinyl acetoacetal, and polyvinyl butyral. Examples of the polyacrylamides include polymers of acrylamides or methacrylamides such as acrylamide, methacrylamide, methylol acrylamide, methylol methacrylamide, diacetone acrylamide or diacetone methacrylamide.

Preferably the hygroscopic resin is cross-linked with a suitable cross-linking agent. If not cross-linked, the hygroscopic resin undergoes a drift phenomenon when subjected to repeated cycles of expansion and contraction according to changes in the humidity of the atmosphere. In other words, the resistance of the humidity-sensitive film 8 in the dry state becomes gradually higher. It is thought that the electrically conductive particles dispersed in the hygroscopic resin 9 move by the influences of expansion and contraction of the resin 9, and even in the dry state, the individual conductive particles are surrounded with the hygroscopic resin thus preventing the conducting particles from contacting one another directly. It is desirable therefore to cross-link the hygroscopic resin with a suitable cross-linking agent and thereby to prevent the movement of the conductive particles within the resin 9. Furthermore, as a result of cross-linking, the hygroscopic resin has resistance to hydrolysis or weathering during use and its durability increases.

The cross-linking agent may be a compound the molecules of which can be bonded chemically with the functional group (hydroxyl) of the hygroscopic resin at 60 to 200°C in the presence or absence of a catalyst. Examples of such a compound are ethylene glycol diacrylate, divinyl benzene, partially methylated methylol melamine, hexamethoxy methylol melamine, phthalic acid, pyromellitic acid, trimellitic acid, acid anhydrides thereof, and epoxy-containing compounds.

The amount of cross-linking agent relative to the hygroscopic resin is 3 to 80% by weight, preferably 5 to 60% by weight, based on the solids content of a solution of the hygroscopic resin. If the amount of the cross-linking agent is too small, the drift phenomenon cannot be prevented. If it is too large, other troubles occur although no drift is caused. For example, the hygroscopicity of the resin is impaired, or the response of the resin to moisture absorption and removal becomes poor, and the speed of response becomes slow. This in turn causes a time lag in the operation of the humidity-sensitive sensor.

Preferably, the thickness of the hygroscopic resin ranges minimum several microns to several hundred microns, especially from several automatic to one hundred and odd microns in order to obtain automobile, strength and a rapid speed of response to changes in the humidity of the atmosphere.

The electrically conductive particles to be dispersed in the hygroscopic resin may be any electrically conductive materials. However, it is preferred to use electrically conductive material having a low coefficient of temperature resistance since it is not desirable that the resistance value of the humidity-sensitive sensor drift according to changes in temperature. Metallic materials having a low inherent resistivity such as silver, gold, aluminum, magnesium, tungsten, molybdenum, cobalt, nickel, chromium, cadmium, platinum, tin, or alloys of the above metals, or inexpensive electrically conductive materials such as graphite, carbon or carborundum (sic) can be used as the conductive materials.

The size of the electrically conductive particles should be determined according to the thickness of the hygroscopic resin. Generally, it is preferred to use particles having a particle size of not more than 100 microns. The amount of the electrically conductive particles should be adjusted so that the sensor has the desired resistance value in view of the size and inherent resistivity of the electrically conductive particles. Generally, a suitable amount is 5 to 1000%, especially 20 to 60%, by volume based on the hygroscopic resin A solution of a hygroscopic resin having dispersed therein the electrically conductive particles for forming the humidity-sensitive film 8 was coated over a pair of the electrodes 6 and 6' and cured by heating to form the sensor 2, and its electric resistance was measured under various conditions. It was found by this test that there was some dispersion in the initial resistance of the sensor produced (the resistance immediately after the curing of the humidity-sensitive film), and the resistance value measured when the sensor was exposed to high humidity conditions and then again returned to a low humidity condition did not correspond with the initial resistance, but usually became higher than the initial resistance. Specifically, it was found that when the sensor produced was exposed to a cycle of high humidity and low humidity conditions at least 30 times, its resistance at a certain temperature approached a certain predetermined value, and when it was exposed more than 50 times, its resistance closely approached the certain predetermined value. It is thought that the above fact can be ascribed to the following cause. That is, in the humidity-sensitive coating immediately after curing, the electrically conductive particles are not uniformly dispersed over the entire area of the hygroscopic resin, but rather the distribution is dense in some parts but sparse in the others. As a result of the repetition of expansion and contraction, the conducting particles in the hygroscopic resin undergoes pressure, and thus, the individual particles are rearranged at stable positions where the above pressure is balanced.

In view of the above fact, it is preferred that the resistance of the sensor should be stabilized by exposing the cured humidity-sensitive coating repeatedly to a cycle of a high humidity condition and a low humidity condition at least 30 times, especially at least 50 times. The high humidity condition and the low humidity condition, as used in this invention, mean a state of humidity higher than the humidity of the atmosphere to be detected by the sensor and a state of humidity lower than such humidity, preferably a state of humidity higher than the maximum humidity of the atmosphere to be detected by the sensor, and the state of humidity lower than the minmum humidity thereof. When the sensor is used in an auutomatic water droplet removing device for a window glass of an automobile, the sensor is repeatedly exposed to a high humidity condition of more than RH 80% and a low humidity condition of less than RH 70%, preferably a high humidity condition of RH 100%, and a low humidity condition of RH less than 60%.

It has been found that when a solution of the hygroscopic resin having dispersed therein electrically conductive particles is cured to form the humidity-sensitive coating, only a very small number of electrically conductive particles are dispersed in the surface layer of the coating as compared with the other parts. Accordingly, a nonsensitive layer the electric resistance of which changes only slightly according to changes in humidity (therefore according to change in the volume of the resin) is formed on the surface layer of the film. The presence of such a non-sensitive layer retards the speed of response of the electric resistance of the humidity-sensitive coating to changes in the humidity of the atmosphere because upon abrupt change in the humidity of the atmosphere, the change in humidity in the part beneath the non-sensitive layer is retarded somewhat as compared with the surface layer. This tendency is especially strong when the atmosphere has a low humidity. It is preferred therefore to remove the surface layer of the cured humidity-sensitive coating 8 and thus to eliminate the non-sensitive layer. When the non-sensitive layer is removed, the resistance value of the humidity-sensitive coating according to changes in relative humidity varies faster. By controlling the amount of the non-sensitive layer removed, the resistance value of the humidity-sensitive coating can be adjusted to the desired value. The removal of the surface layer of the humidity-sensitive coating can be carried out mechanically and/or chemically. For example, it can be removed by mechanical shaving with sand paper or steel wool, or chemically with citric acid having a concentration of less than 10%. Preferably, this removing operation is performed while measuring the electric resistance between the two electrodes of the sensor so that the resistance value is adjusted to the desired value. The measurement of the electric resistance between the electrodes of the sensor must be performed after removing the shaving dust with, for example, methyl alcohol, and drying the film. This is because the shaving dust contains electrically conductive particles which affect the electric resistance.

Another embodiment of this invention will be described below with reference to FIGS. 3 and 4. In the humidity-sensor 2 shown in FIGS. 1 and 2, a solution of the hygroscopic resin having dispersed therein electrically conductive particles is directly coated on base plate 4 to form the humidity-sensitive coating 8. Bond strength between the coating 8 and the base plate is sometimes not sufficient. Furthermore, since the coating 8 comes in direct contact with the electrodes 6 and 6', it is necessary to select materials which do not affect each other. Furthermore, it is usually necessary to cure the coated resin layer in an electric furnace after drying in the air. However, if the base plate is, for example, a rear window of an automobile, the entire rear window must be placed in an electric furnace in order to cure only a part of it on which the resin film has been coated. Accordingly, the use of a large-sized electric furnace is required, and thermal efficiency is reduced. In the embodiment shown in FIGS. 3 and 4, a cured humidity-sensitive coating is bonded to the base plate and the electrodes through an adhesive layer whereby the above-mentioned various disadvantages can be eliminated.

Figure 3:
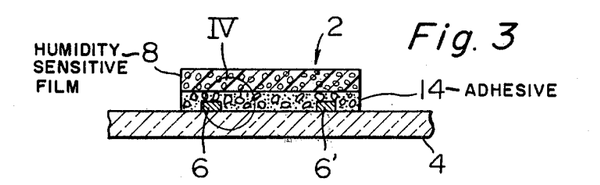
FIG. 3 is a sectional view of another embodiment of the humidity-sensitive sensor in accordance with this invention.
Figure 4:
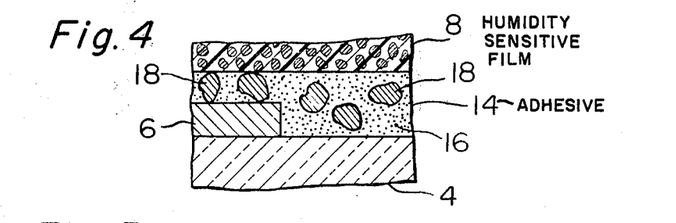
FIG. 4 is an enlarged sectional view of portion IV of FIG. 3.

Referring to FIGS. 3 and 4, the humidity-sensitive sensor 2 consists of a pair of metallic electrodes 6 and 6' disposed in spaced relationship and fixed to a base plate 4 such as a window glass of an automobile by, for example, baking, and a humidity-sensitive coating 8 bonded to the electrodes 6 and 6' and the base plate 4 by means of an adhesive layer 14. The humidity-sensitive coating 8 is the same as that described above with reference to FIGS. 1 and 2.

The adhesive layer 14 should serve not only to bond the humidity-sensitive coating 8 to the electrodes 6 and 6' and the base plate 4, but also to connect the electrodes 6 and 6' electrically to the humidity-sensitive film 8 and maintain the space between the electrodes 6 and 6' in a substantially, electrically non-connective state. To achieve this end, the adhesive layer 14 is composed of a non-conductive adhesive 16 and a number of electrically conductive particles 18 dispersed therein.

The adhesive 16 may be any non-conductive adhesive, but the use of non-hygroscopic adhesives, for example, those of the epoxy, cyan or acrylic type, is preferred, because hygroscopic adhesives affect the accurate response of the sensitive coating 8 to the humidity of the atmosphere as a result of absorbing moisture.

The electrically conductive particles 18 may, for example, be of metals, carbon, carbides, silicides, nitrides, or borides. The shape of the conductive particles 18 is optional, for example, circular, acicular or spherical. As shown in FIG. 4 on an enlarged scale, the electrically conductive particles have a portion larger than the thickness of the portion of the adhesive layer between the electrode and the humidity-sensitive coating so as to connect the electrodes and the humidity-sensitive coating electrically. Furthermore, in order to avoid substantial short-circuiting between the electrodes 6 and 6', these electrically conductive particles 18 are dispersed in such a manner that they are discontinuous over the area between the electrode 6 and the electrode 6' even when they partially come in contact with one another, and preferably the individual particles are not in contact with one another.

When bonding the humidity-sensitive coating 8 to the electrodes 6 and 6' and the base plate 4 by the adhesive layer 14, it is preferred to coat an adhesive 14 containing electrically conductive particles 18 dispersed therein on the electrodes and base plate in a relatively thin layer, place the humidity-sensitive coating 8 on the adhesive layer so formed, and apply pressure to this assembly from above to extrude the excessive adhesive from between the electrodes and the humidity-sensitive coating to attain the state as shown in FIG. 4.

The thickness of the adhesive layer is about 8 to 100 microns between the base plate 4 and the coating 8. It should not be so thick that the distance between the humidity-sensitive coating 8 and the base plate 4 becomes large and there is a substantial difference in temperature and/or humidity between the film 8 and the base plate 4, and should not be so thin that the required bond strength cannot be obtained. Where the humidity-sensitive coating 8 is bonded through the adhesive layer 14, the coating 8 is spaced from the base plate 4 by the distance corresponding to the thickness of the adhesive layer. Accordingly, it is preferred to reduce the thickness of the humidity-sensitive coating 8 to a thickness of from 8 to 50 microns.

It was found that when a graphite powder having a particle size of 125 mesh was dispersed in a commercially available epoxy-type adhesive (tradename, ARALDITE, a product of Ciba Geigy) in a weight ratio of 1:1, and the humidity-sensitive coating was pressed against the resulting adhesive layer, not only the space between the electrodes and the humidity-sensitive coating but also the space between the both electrodes became conductive and had a low resistance. When the weight ratio of the graphite powder was changed to 0.5:1 based on the adhesive, the space between the electrodes and the humidity-sensitive coating became conductive with a low resistance, but the space between the two electrodes was substantially non-conductive and the resistance became as high as more than 2 megaohms/square. When the weight ratio of the graphite was further reduced to 0.2:1 based on the adhesive, the space between the electrodes and the humidity-sensitive coating became conductive and had a low resistance, and the space between the two electrodes exhibited an infinitely high resistance.

Figure 5:
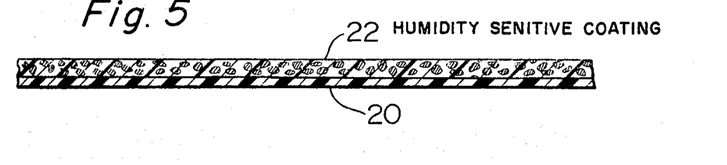
FIG. 5 is a sectional view of a humidity-sensitive film formed on a thin plastic sheet.

One preferred method for curing the sensitive coating and then bonding it to a suitable substrate through an adhesive layer will be described. First, a solution of a hygroscopic resin having dispersed therein electrically conductive particles is coated in a suitable thickness on a relatively large-sized thin plastic sheet 20 as shown in FIG. 5. It is preferred that as the thin plastic sheet 20, a material, such as a thin polycarbonate sheet, which has weak adhesion to the hygroscopic resin, be used. After the coating on the plastic sheet 20 has been dried, it is placed, for example, in an electric oven, and heated to cure the coating of the hygroscopic resin thereby to form a humidity-sensitive coating 22 on the plastic sheet 20. The plastic sheet having the humidity-sensitive coating 22 so formed is then cut to the desired size. If desired, the humidity-sensitive coating can be exposed to a repetition of the high humidity and low humidity states before or after cutting as described above. Then, an adhesive containing electrically conductive particles dispersed therein is coated on a base plate on which a pair of electrodes are baked or on the surface of the sensitive coating 22 cut to the desired size to bond the sensitive coating 22 formed on the thin plastic plate 20 to the pair of electrodes and the base plate. After the adhesive has been fully cured, the thin plastic plate is removed from the sensitive coating 22, to attain the state shown in FIG. 3. Furthermore, it is preferred to shave off the surface of the sensitive coating from which the plastic plate has been removed.

In such a method, the adhesion between the sensitive coating and the base plate is higher than that between the sensitive coating and the plastic base plate, and therefore, it is necessary to removed only the plastic sheet after bonding the sensitive coating to the base plate. In order to achieve this, it is preferred to use a thin plastic sheet only weakly adherent to the humidity-sensitive coating and maintain the atmosphere at a relative humidity of not more than 75%, preferably not more than 65%, during the curing of the adhesive between the sensitive coating and the base plate. Our experience shows that if the relative humidity of the atmosphere is more than 75% at the time of curing the adhesive, attempt to removed the thin plastic sheet after the curing of the adhesive results in the separation of the sensitive coating from the base plate, and if the relative humidity of the atmosphere is less than 65%, the adhesion between the sensitive coating and the base plate is sufficiently larger than that between the sensitive coating and the thin plastic sheet.

Figure 6:
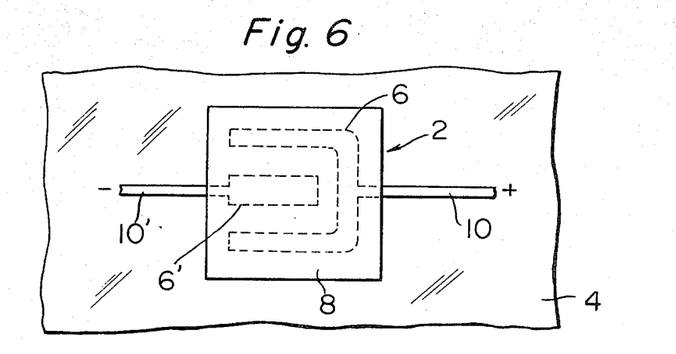
FIGS. 6 and 7 are each a plan view of the humidity-sensitive sensor in accordance with this invention equipped with electrodes having shapes desirable for preventing electric corrosion.
Figure 7:
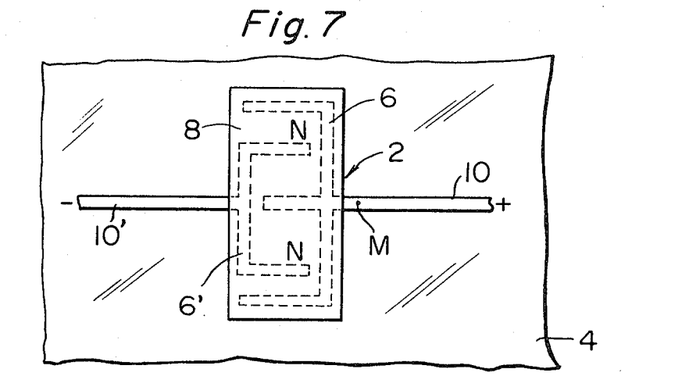

Now, referring to FIGS. 6 and 7, there are shown further embodiments of this invention in which the electrolytic corrosion of electrodes is prevented by modifying the shape of the electrodes.

In the humidity-sensitive sensor in accordance with this invention, electrodes of silver or nichrome are usually used because of their cost, processability and stability. When a direct current potential is applied between electrodes of silver or nichrome, the silver or nichrome is dissolved by the moisture to cause what is called electrolytic corrosion, in which case the life of the sensor depends upon the life of the electrode. Our investigations concerning this electrolytic corrosion have revealed that generally, a part covered with the sensitive coating or adhesive layer undergoes little electrolytic corrosion, but electrolytic corrosion is great at a portion directly exposed to the atmosphere (that is, the lead portion). It was further found that the electrolytic corrosion is great at the lead portion of the positive electrode, especially that part of the lead portion which is near the negative electrode, and also, the electrolytic corrosion is greater when the sensitive sensor is exposed to a higher humidity condition. As regards such a phenomenon, it is thought that when the humidity-sensitive sensor is exposed to a very high humidity condition for a long time, the material of the positive electrode is ionized and the ions move towards the negative electrode along the potential gradient through the moisture layer on the surface of the base plate and are precipitated there, whereby electrolytic corrosion occurs. It is also thought that the reduced electrolytic corrosion at the portion covered with the sensitive coating or adhesive layer as compared with the portion exposed to the atmosphere is due to the fact that even when the material of the positive electrode is ionized, the ions cannot move to the negative electrode unless they pass through the humidity sensitive coating or the adhesive layer, and this sensitive coating or adhesive layer prevents the movement of the ions.

In view of the above fact, it is desirable to inhibit the electrolytic corrosion of the electrodes by increasing the length of the path between the lead portion of the positive electrode directly exposed to the atmosphere and the corresponding portion of the negative electrode so that it does not go through the equal potential portion of the positive electrode. One example of achieving this end is to build the positive electrode 6 in a C-shape to surround the forward end of the negative electrode 6'. By this arrangement, the length of the path between the lead portion 10 of the positive electrode exposed directly to the atmosphere and corresponding portion of the electrode which path does not go through the equal potential portion of the positive electrode becomes long, and therefore, the electrolytic corrosion of the portion 10 directly exposed to the atmosphere is restricted. In the sensor 2 shown in FIG. 7, the negative electrode 6' is formed in a C shape, and the positive electrode 6 is formed in an E shape so that each end of the negative electrode 6' is surrounded by a corresponding end of the positive electrode. In the embodiment shown in FIG. 7, too, the length of the path between the lead portion 10 of the positive electrode directly exposed to the atmosphere and the negative electrode which path does not go through the equal potential portion of the positive electrode becomes long, and the electrolytic corrosion of the lead portion 10 is inhibited.

Electrolytic corrosion can also be inhibited by using a difficulty ionizable metal such as gold, platinum, palladium, rhodium or an alloy of such a metal as a material for forming that part of the lead portion 10 which is directly exposed to the atmosphere which is near the negative portion, for example, a portion in which the distance running from the lead portion 10' of the negative electrode directly exposed to the atmosphere to the lead portion 10 of the positive electrode not directly exposed to the atmosphere without going through the humidity-sensitive coating is not more than 5 cm, preferably not more than 10 cm.

Furthermore, electrolytic corrosion occurs with more difficulty when the humidity-sensitive coating 8 is bonded to the base plate 4 via the adhesive layer 14, especially a hydrophobic adhesive layer, as shown in FIG. 3 than when the sensitive coating 8 is directly bonded to the base plate 4 without the intermediary of an adhesive layer as shown in FIG. 2. In this regard, too, it is preferred to bond the sensitive coating 8 to the basic plate through the adhesive layer 14. The inhibition of electrolytic corrosion by the use of the adhesive layer 14 is considered to be due to the fact that the adhesive layer 14 prevents the intrusion of moisture into the surface of the electrodes and thus leads to the inhibition of the ionization of the electrode materials.

Figure 9:
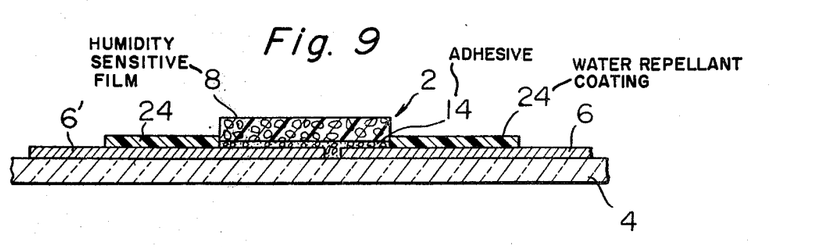
FIG. 9 is a sectional view taken along the line IX—IX of FIG. 8.
Figure 10:
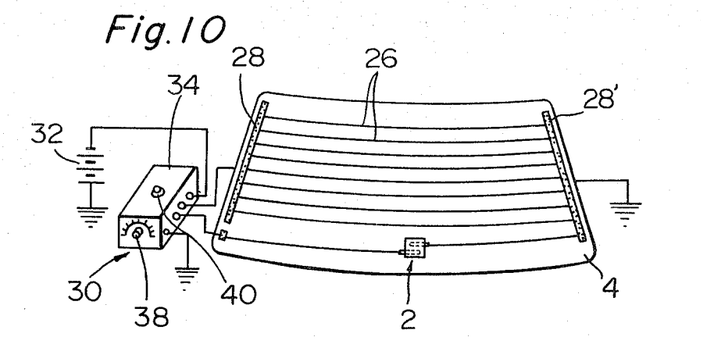
FIG. 10 is a simplified view of an automatic water droplet removing apparatus for a rear window glass of an automobile which is equipped with the humidity-sensitive sensor in accordance with the present invention.

In order to prevent the electrolytic corrosion of that portion of the electrode which is directly exposed to the atmosphere more effectively, it is preferred to coat a water-repellent substance 24 on the surface of the base plate near the sensitive coating and/or the lead portion of the electrode other than the part coated with the sensitive coating 8 or the adhesive layer 14, as shown in FIGS. 9 and 10. By the coating of the water-repellent substance, the ionization of the lead portion of the positive electrode and the movement of the ions to the negative electrode can be effectively prevented even in a high humidity condition. The water-repellent substance is preferably one which has a contact angle of at least 50° when in contact with water. Examples of the water-repellent substance are silicone oils, ordinary oils, or solutions of alkylpolysiloxanes in organic solvents commercially available as repellents for window glass of automobiles under the tradename RAIN-X (a product of Unelko Co.) or Q-BALL 100. In practice, it is preferred to coat the water-repellent substance on the surface of the base plate and the lead portion of the electrode over a distance of 30 mm, preferably within 50 mm, from the end of the sensitive sensor.

Now, referring to FIG. 10, an automatic water droplet removing device for rear windows of automobiles using the humidity-sensor in accordance with this invention will be described with reference to FIG. 10.

Figure 11:
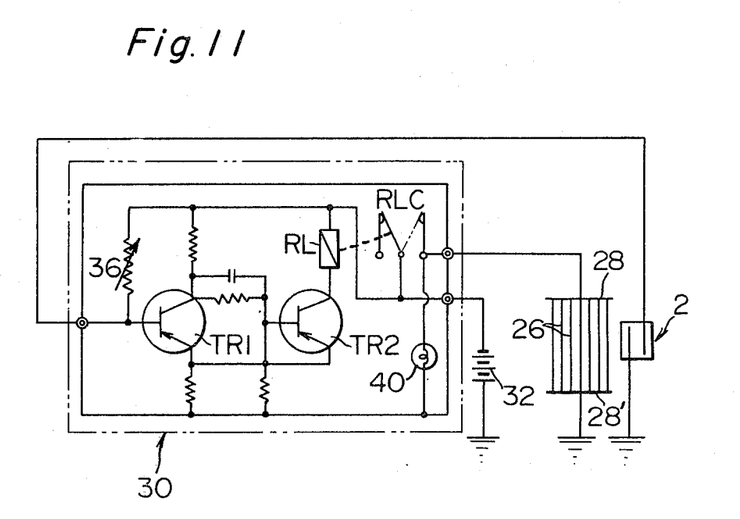
FIG. 11 is a circuit in the automatic water droplet removing apparatus of FIG. 10.

This automatic water droplet removing device includes heating means composed of a plurality of resistance wires bonded to a rear window glass 4 by, for example, baking, a pair of common electrodes 28 and 28′ to which the end of each resistance wire 26 is connected, a humidity-sensitive sensor 2 in accordance with this invention, a control device 30 for controlling the supply of power to the heating means according to changes in the electric resistance of the sensitive sensor 2, and a battery 32 (for example, 12V) carried on an automobile. The control device 30 possesses a housing 34 made of an electrically conductive material such as metal. As shown in FIG. 11, thus housing 34 contains a Schmidt circuit including two transistors TR1 and TR2, a relay RL having a relay contact RLC, a variable resistor 36 having a knob 38 projecting externally of the housing 34 (see FIG. 10), and a pilot lamp 40 which is switched on when electric current is being supplied to the heating means.

Referring to FIGS. 10 and 11, the operation of the automatic water droplet removing device will be described briefly. When the relative humidity of the atmosphere surrounding the humidity-sensitive sensor 2 is low (therefore, when water droplets do not adhere to the surface of the glass inside the automobile in considerable amounts), the resistance of the sensor 2 is low, and the base bias voltage of the transistor TR1 is higher than the emitter voltage, at which time the transistor TR2 is "on". Hence, current flows through the collector of the transistor TR2 to energize the relay RL, and the relay contact RLC is positioned on the left side as shown by a solid line in FIG. 11. In this condition, the electric current is not supplied to the heating means. When the relative humidity of the atmosphere surrounding the sensor 2 becomes high (therefore, when a considerable amount of water droplets has adhered to the surface of the glass inside the automobile), the resistance of the sensor 2 becomes high, and the base bias voltage of the transistor TR1 becomes lower than the emitter voltage, at which time the transistor TR1 is in the cut-off state. Hence, the collector current of the transistor TR2 is shut off, and the relay RL is deenergized and positioned on the right side as shown by a two dotted chain line shown in FIG. 11. Thus, electric current is supplied to the heating means thereby to heat the glass. When as a result of heating the glass, the water droplets adhering to the surface of the glass are evaporated and the resistance of the sensor 2 is reduced, the transistor TR2 again assumes the "on" state and the supply of current to the heating means is stopped. By adjusting the resistances of the variable resistor 36, the supply of current to the heating means and its shutting off can be automatically controlled with a predetermined relative humidity as a boundary.

Since the sensor in accordance with this invention has an especially high sensitivity in the medium and high humidity ranges, it is easy to supply current to the heating means using an amplifier of low gain before the rear window fails to permit an outside view. Accordingly, by means of a relatively inexpensive automatic water droplet removing device, the rear window can be maintained always in the viewable condition.

The following Examples illustrate the present invention more specifically.

EXAMPLE 1

A pair of metal electrodes each having a length of 20 mm and a width of 1 mm and having the shape as shown in FIGS. 1 and 2 were baked on a small piece of glass plate with a distance of 10 mm between them. To a methyl cellosolve solution of a copolymer of hydroxyethyl methacrylate and methyl methacrylate was added 2% by weight, based on the solids content of the solution, of methylol melamine (tradename UFORMITE; MM-83, a product of Rohm & Haas) as a cross-linking agent, and 30% by volume, based on the solids content of the solution, of graphite powder having an average particle size of 30 microns was added as electrically conductive particles. The resulting solution was coated over the area between the electrodes, and heat-treated for 30 minutes in an atmosphere held at 120°C. to cure it and form a humidity-sensitive coating having a thickness of 30 microns. The resulting product was designated Sample 1A for the measurement of resistance-humidity charateristics.

Separately, a gold coating was formed on a small piece of glass plate by vacuum deposition, and the same resin solution as above except containing no graphite powder was coated on the gold coating and cured to form a resin coating having an area of 100 mm². Then, a porous gold coating was formed on this resin by vacuum deposition thereby to form a resin coating interposed between a pair of gold coatings. The resulting product was designated Sample 1B for the measurement of change in volume.

A lead wire was attached to each of the Samples 1A and 1B. Sample 1A was connected to a resistance measuring instrument, and Sample 1B, to a capacity measuring instrument. Then, both of these samples were fixed in a constant-humidity bath.

Figure 12:
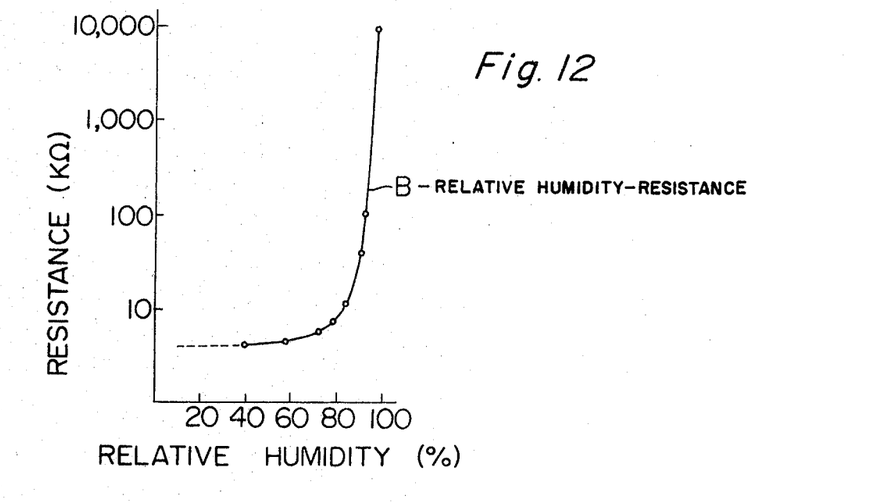
FIG. 12 is a graphic representation showing the relation between the relative humidity and the resistance of the humidity-sensitive sensor described in Example 1 of this application.

The temperature within the constant-humidity bath was maintained at 30°C., and the relative humidity was raised. When the humidity was 40%, the resistance of Sample 1A was about 4 KΩ. When the humidity in the bath was raised to 59%, 73%, 79%, 91%, 93%, and 97%, the resistance of the Sample 1A changed to 4.5 KΩ, 5.7 KΩ, 7.5 KΩ, 12 KΩ, 43 KΩ, 100 KΩ, and 10000 KΩ, respectively. The resistance-relative humidity relation of Sample 1 is shown in FIG. 12. It can be seen from the results obtained that when the humidity was raised by 57% from 40 % to 97%, the resistance of Sample 1A rose to 2500 times.

Furthermore, from the measurement of the interelectrode capacity of Sample 1B in response to changes in relative humidity, it was found that at a relative humidity of 97%, the resin coating swells by about 35% of its volume at a relative humidity of 40%.

EXAMPLE 2

A pair of electrodes of the shape shown in FIGS. 1 and 2 each having a width of 1 mm and a length of 40 mm were baked on a small piece of glass plate using a silver paste with the distance between the electrodes being kept at 7 mm. To a 18% by weight methyl cellosolve solution of 2-hydroxyethyl methacrylate as a hygroscopic resin were added 90% by weight, based on the solids content of the solution, of partially methylated methylol melamine as a cross-linking agent and a tiny amount of trifluoroacetic acid as a catalyst. Furthermore, as electrically conductive particles 4, 50% by weight, based on the solids content of the solution, of graphite powder having a particle size of about 20 microns was added. The resulting coating solution was coated on the small piece of glass plate, and heat-treated at 100°C. for 1 hour to cure it and thus form a humidity-sensitive coating 3. The resulting product was designated Sample 2A.

Samples 2B, 2C, 2D and 2E were prepared in the same way as above except that the amount of the cross-linking agent was changed to 50, 20, 2, and 0% by weight respectively.

Lead wires were fitted to the electrodes of each of the above samples, and connected to a power source (direct current 12V) and a current self-recording means. Then, each of the samples was suspended in a chamber in which warm water at 50°C. was stored. Air was blown laterally against the samples using a fan which was operated for 5 minutes at intervals of 10 minutes by means of a timer. During this repeated operation, the current passing through the samples was recorded. Each of the samples was exposed to steam at 50°C. for 10 minutes, and for the next 5 minutes, the supply of steam was shut off by the operation of the fan to remove the steam absorbed in the humidity-sensitive coating. This cycle was repeated continuously using the timer. As a result of the repetition of the moisture absorption-removal cycle, the sample 2A in the moisture-absorbed absorbed state had a resistance value about 2.0 times that in the moisture-removed state. On the other hand, the current flowing through the samples 2B, 2C, 2D and 2E in the moisture-absorbed state is almost infinite (about 2 MΩ for the resistance of the sensor), and the resistance value at the time of moisture removal was about 4 KΩ in the early stage. As the cycle was repeated, however, the resistance was gradually reduced. After 200 cycles for Sample 2E and 500 cycles for Sample 2E, there was hardly any change in electric current in the moisture absorbed and removed states. With Samples 2C, 2B and 2A, however, there was no large reduction in electric current as compared with the initial electric current value, and even after about 3,000 cycles, there was a large difference in the electric current value between the moisture absorbed state and the moisture removed state. Thus, these samples exhibited sufficient sensitivity to function as sensors. On the other hand, the time required from the time when the sensor absorbed moisture and attained a high resistance (low electric current) until it was deprived of moisture and attained a low resistance (high electric current) (that is, the speed of response) was 10 seconds for Sample 2E, 15 seconds for Sample D, 25 seconds for Sample C, 90 seconds for Sample B, and 4 minutes for Sample A. The speed of response differs according to the usage, but generally, those having a high speed of response are preferred.

EXAMPLE 3

A pair of electrodes of the shape shown in FIGS. 1 and 2 each having a width of 1 mm were baked on a small piece of glass plate using a silver paste with the distance between the electrodes being adjusted to 5 mm. To a 18% methyl cellosove solution of polymer of 2-hydroxyethyl methacrylate as a hygroscopic resin were added 8% by weight, based on the solids content of the solution, of methylolated methoxymelamine as a cross-linking agent, a tiny amount of hydrochloric acid as a catalyst, 20% by weight, based on the solids content of the solution, of a nonionic surface active agent (EMULGEN 903, tradename), and about 50% by weight, based on the solids content, of graphite particles having a particle diameter of about 20 microns. The resulting coating solution was coated on the surface of a small piece of glass to cover the electrodes, and cured at 130°C. for 30 minutes to form a humidity-sensitive coating.

The resulting coating was exposed to about 20,000 cycles of a low humidity condition of 60% relative humidity at 30°C. and a high humidity condition of 95% relative humidity at 30°C. The initial electric resistance between the electrodes of this sensor was about 1.5 KΩ at 30°C. and a relative humidity of 60%.

Figure 13:
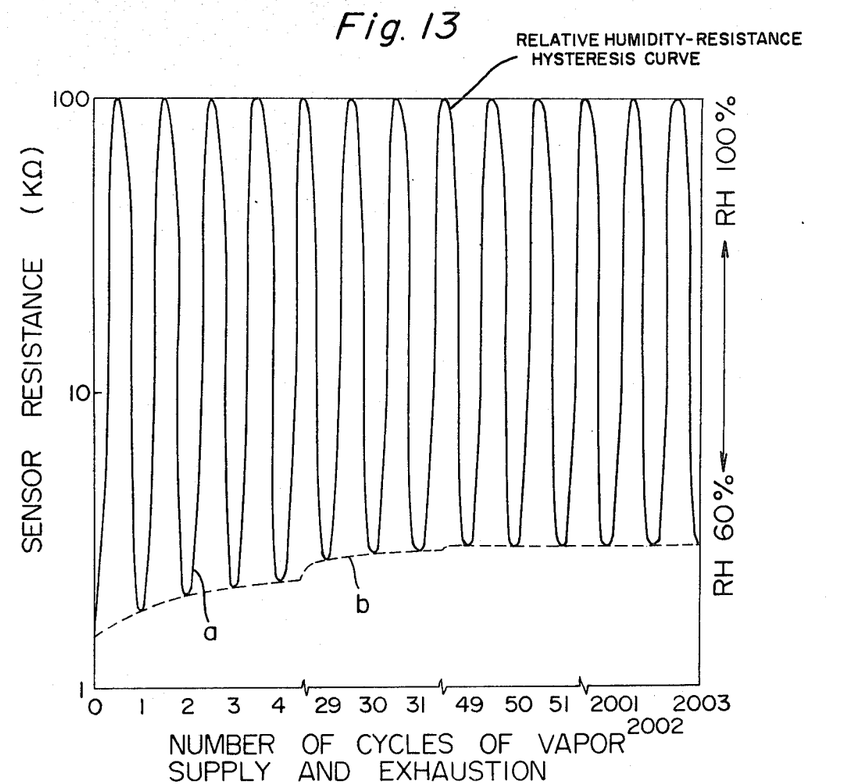
FIG. 13 is a graphic representation showing the changes in electric resistance when the humidity-sensitive sensor described in Example 3 of this application was exposed repeatedly to the high humidity state and to the low humidity state.

The sensor was exposed to steam at 30°C. and a relative humidity of 95% or more, and then again exposed to an atmosphere at 30°C. and a relative humidity of 60%, and the resistance was found to be about 1.8 KΩ. This was a 20% increase over the initial resistance. However, when it was repeatedly exposed to steam at 30°C. and a relative humidity of at least 95% and an atmosphere at 30°C. and a relative humidity of 60%, the sensor had a resistance of 2.8 KΩ after 30 cycles and 3.0 KΩ after 50 cycles. Even after 20,000 cycles of the high humidity condition-low humidity condition, the electric resistance was 3.0 KΩ. This change in resistance is shown in FIG. 13. FIG. 13-a shows the changes in resistance when a cycle of a high humidity condition (a relative humidity of at least 95%) and a low humidity condition (a relative humidity of 60%) was repeated at 30°C. FIG. 13-b shows the resistance values of the sensor in the low humidity condition in each cycle.

FIG. 13 thus demonstrates that the sensor exposed to 30 cycles of a high humidity condition and a low humidity condition had an interelectrode resistance of 2.8 KΩ in the low humidity state (a relative humidity of 60%); and that during use, the resistance in the low humidity condition sometimes rises to 3 KΩ, but the increase in resistance is only 7%, which shows very stable performance of the sensor since the resistance increase was 100% [(3.0 − 1.5)/1.5 = 1.00] when this repeating treatment was not performed.

EXAMPLE 4

Figure 8:
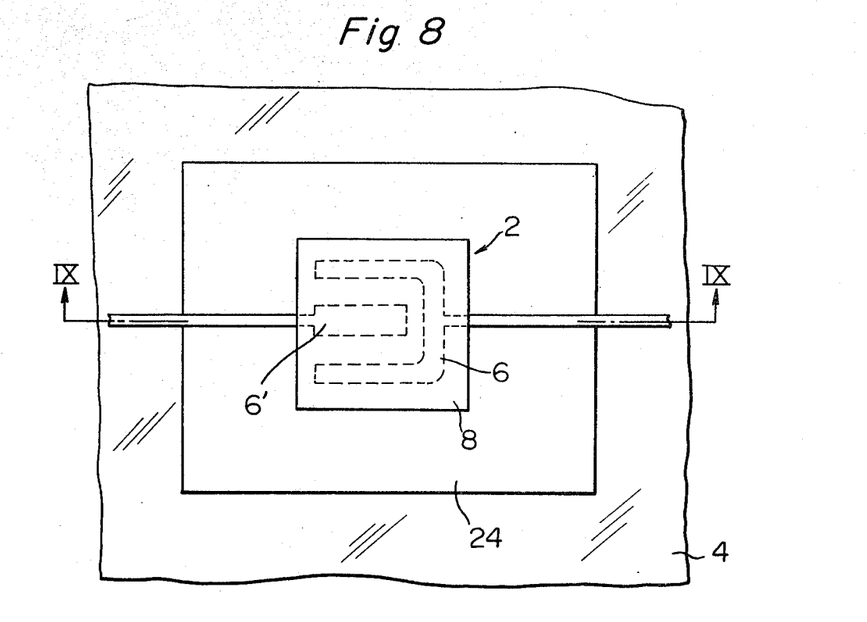
FIG. 8 is a plan view of the humidity-sensitive sensor coated with a water-repellent substance for the prevention of electrolytic corrosion.

A pair of electrodes of the shape shown in FIG. 8 were baked on a small piece of glass plate using a silver paste, and a mixture of an epoxy adhesive (tradename ARALDITE) and gold powder in a weight ratio of 1:0.5 was coated in a thin layer over the electrodes.

To a 18% by weight methyl cellosolve solution of a polymer of 2-hydroxyethyl methacrylate as a hygroscopic resin were added 6% by weight, based on the solids content of the solution, of an epoxy cross-linking agent (tradename, ERL 4221, a product of Union Carbide), and 30% by volume, based on the solid content of the solution, of graphite particles having an average particle size of 30 microns. The resulting coating solution was coated on a polycarbonate sheet, dried, and cured for 30 minutes in an electric furnace at 130°C. thereby to form a humidity-sensitive coating thereon. Then, the polycarbonate sheet was cut to a suitable size. The top surface of the sensitive coating was urged against the adhesive layer on the small piece of glass, and after hardening of the adhesive layer, the polycarbonate sheet was peeled off, whereupon a 25 micron thick humidity-sensitive coating 6 was transferred onto the glass. The resulting sensor was designated Sample 4A.

On the other hand, the surface layer of the sensitive coating on the side facing the atmosphere was shaved off to a thickness of about 1 to 2 microns by means of a steel wool. The resulting product was designated Sample 4B.

Figure 14:
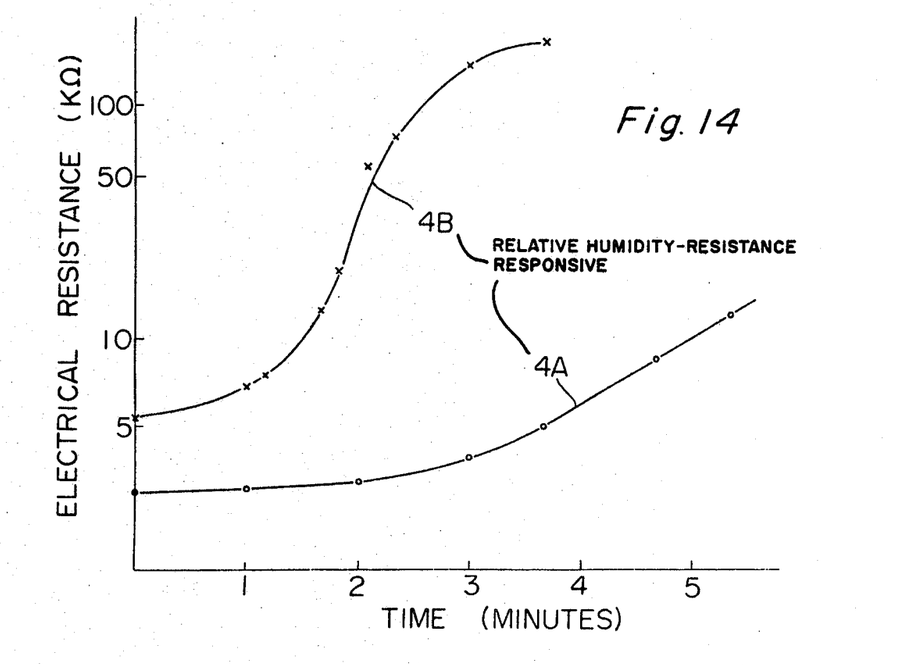
FIG. 14 is a graphic representation showing the relation between the changes in resistance and the time in the humidity-sensitive sensor described in Example 4 of this application.

Samples 4A and 4B were set in a constant temperature-humidity bath in which the atmosphere was maintained at 0°C. and a relative humidity of 50%. Then, the door of the bath was opened abruptly to expose the inside of the bath to the outer atmosphere (temperature 20°C., relative humidity 75%). At this moment, water was condensed and gathered on the surface, and the relative humidity was maintained at 100%C. While maintaining the relative humidity in the bath at 100%, the temperature of the bath was maintained at less than 10°C. FIG. 14 shows changes in the electric resistance of Samples 4A and 4B which began immediately after the opening of the door of the bath as described above. In FIG. 14, curve 4A refers to the change of the electric resistance of Sample 4A, and curve 4B, to that of Sample 4B. It is seen from FIG. 14 that Sample 4A in which the surface layer of the sensitive coating was not shaved off exhibited a resistance increase of about 1.5 times after 3 minutes from the abrupt change in humidity, and a gradual increase in electrical resistance was observed after a lapse of 5 minutes; but the Sample 4B showed a resistance increase of about 20 times after 3 minutes, and the resistance value was almost constant after 3 minutes. This means that Sample 4B had a faster speed of response and a larger rate of change in electric resistance than Sample 4A.

Twenty pieces each of Samples 4A and 4B were produced, and the electric resistance values of these samples were measured. As a result, it was found that the electric resistances of Samples A and B were $3.0 \pm 2$ K$\Omega$ and $6.0 \pm 1$ K$\Omega$ respectively at a relative humidity of 50%. This shows that with sample 4B, dispersion of the electric resistance was lower than Sample 4A.

EXAMPLE 5

A negative electrode having a C-shaped tip and a positive electride having an E-shaped tip so as to surround the tip of the negative electrode as shown in FIG. 7 were coated and baked on a cleaned glass sheet having a size of 100 mm × 300 mm and a thickness of 5 mm using a silver paste so that the width of the electrically conductive portion was 1 mm. The same humidity-sensitive coating as in Example 1 was directly formed on the glass plate so as to cover the tip portions of these electrodes to produce a humidity-sensitive sensor (Sample 5A).

Figure 15:
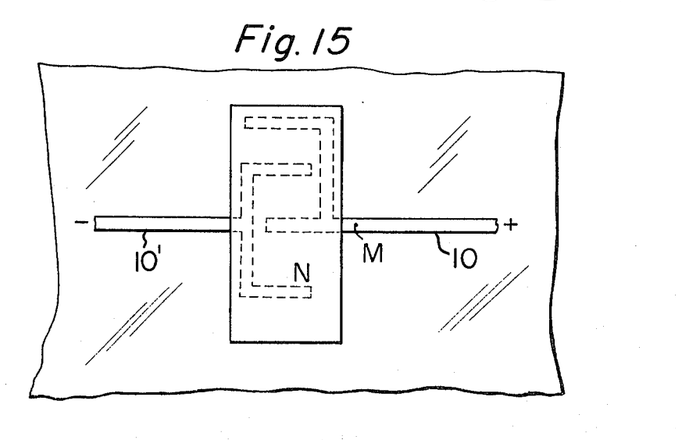
FIG. 15 is a plan view of the humidity-sensitive apparatus used in Examples 5 to 7 of this application.

Separately, positive and negative electrodes having a C-shaped tip as shown in FIG. 15 were coated and baked on a cleaned glass plate of the same size as the glass plate used above by means of a silver paste so that the width of the electrically conducting part became 1 mm. The same sensitive coating as described above was formed directly on the glass plate so as to cover the tip portions of the electrodes (Sample 5B for comparison).

Lead wires were attached to the electrodes of each of Samples 5A and 5B, and the Samples were set in a constant temperature bath held at 25°C. and a relative humidity of at least 95%. The lead wires of each of these samples were connected to a power source (direct current 100 V) through an ammeter. After a lapse of about 24 hours, the positive electrode in Sample 5B began to turn blackish, and after about 72 hours, the wires were broken. On the other hand, in the Sample 5A, no change was observed until the period of about 100 hours passed, but after 300 hours, the wires were broken. Since in Sample 5A, the E-shaped electrode has a point with a potential equal to the potential at point M between the portion M of the positive electrode exposed to the atmosphere and the tip N of the negative electrode, the electrode material that has been ionized at point M has difficulty in moving to the point N (namely, the movement of the ions from the positive electrode to the negative electrodoe is difficult), whereby an effect of inhibiting electrolytic corrosion is obtained.

On the other hand, in Sample 5B, it is not necessary to go through a point having an equal potential to the point M when the ions move from that portion M of the positive electrode which is exposed to the atmosphere to one end N of the negative electrode 8 via the humidity-sensitive coating. Therefore, electric current is more easily caused to flow between M and N through the moisture adhering to the glass plate, and the ionized positive electrode material moves towards N thereby to cause electrolytic corrosion.

EXAMPLE 6

A negative electrode having a C-shaped end and a positive electrode having an E-shaped end surrounding the end of the negative electrode as shown in FIG. 7 were coated and baked on a cleaned glass plate having a size of 100 mm × 300 mm and a thickness of 4 mm using a silver paste so that the width of the electrically conductive portions of the electrodes became 1 mm. An adhesive layer consisting of a commercially available instantaneous adhesive (tradename ARONAL-PHA, a product of Toa Gosei Chem. Co.) and a 325-mesh gold powder in a weight ratio of 1:0.2 was coated so as to cover the ends of both electrodes. The resulting humidity-sensitive sensor was designated Sample 6A.

Positive and negative electrodes having a C-shaped end as shown in FIG. 15 were coated and baked on a cleaned glass plate having the same size as above using a silver paste so that the width of each of the electrodes was 11 mm. The same humidity-sensitive coating as above was bonded so as to cover the end portions of the electrodes to form a product designated Sample 6B.

These Samples 6A and 6B were subjected to the same electrolytic corrosion test as in Example 5. It was found that in Sample 6B, the positive electrode began to turn blackish after about 24 hours, and after about 72 hours, the wires were broken. On the other hand, in the case of Sample 6A, there was scarcely any change even after 1000 hours, and after 2000 hours, the positive electrode turned slightly blackish.

EXAMPLE 7

In the Samples 6A and 6B used in Example 6, the portion which runs 50 mm (in the right hand direction in FIG. 7 or 15) from the branching point of the positive electrode was replaced by a platinum-palladium alloy. The resulting products were designated Samples 7A and 7B. When the Samples 7A and 7B were subjected to the same electrolytic corrosion test as in Example 5, it was found that in Sample 7A, almost the same current as the initial current flowed even after 2000 hours, and the positive electrode did not turn blackish. But in the case of Sample 7B, the positive electrode was broken after 70 hours.

EXAMPLE 8

A pair of electrodes having the shape shown in FIG. 1 each having a width of 1 mm and a length of 154 mm with the length of the facing portion being 4 mm and the distance between the electrodes at the facing portion being 4 mm were baked on a cleaned glass plate having a size of 100 mm × 300 mm and a thickness of 5 mm using a silver paste. To a 18% by weight methyl cellosolve solution of a polymer of 2-hydroxyethyl methacrylate were added 10% by weight, based on the solids content of the solution, of pyromellitic acid as a cross-linking agent and a tiny amount of trifluoroacetic acid as a catalyst for the crosslinking reaction. The resulting solution was coated over the electrodes and coated and cured to form a humiditysensitive coating. A water-repellent (RAIN-X, tradename) consisting of an alkylpolysiloxane in an organic solvent was impregnated in a gauze fabric and coated on the surface of the glass plate and the electrodes at parts other than that coated with the sensitive coating to thereby form a humidity-sensitive sensor. The resulting sensor was designated Sample 8A. On the other hand, the Sample 8A before the formation of the water-repellent layer was designated Sample 8B.

In the open portion of an open-topped refrigerator box, two Samples 8A and 8B were placed with the surfaces of the sensors facing upwards, and the temperature of the refrigerator box was set at −20°C. Lead wires were attached to the electrodes of each of the Samples and connected to a power source (direct current 6 V), and with continued current flowing, a corrosion resistance test was performed. At this time, the temperature of the room was maintained at 20°C. and a relative humidity of 60 to 65%.

As a result, the sample 8B turned slightly blackish at the positive electrode portion, and was broken on the third day, showing the occurrence of complete electrolytic corrosion. On the other hand, in the case of Sample 8A, no change was seen in the electrodes even after a lapse of 30 days.

What is claimed is:
1. A humidity-sensitive sensor comprising:
    an electrically non-conductive base plate;
    a pair of spaced electrodes fixed on said base plate;
    a humidity-sensitive coating composed of a hygroscopic resin having dispersed therein electrically conductive particles and extending over said pair of electrodes; and
    an adhesive layer bonding said humidity-sensitive coating to said base plate, said adhesive layer being composed of an adhesive having dispersed therein electrically conductive particles and electrically connecting each of said electrodes to said humidity-sensitive coating while electrically insulating said electrodes from each other.
2. The sensor of claim 1 wherein said adhesive is non-hygroscopic.
3. The sensor of claim 2 wherein the volume of the electrically conductive particles dispersed in the hygroscopic resin is 20 to 60% of that of the hygroscopic resin.
4. The sensor of claim 3 wherein said hygroscopic resin is a resin taken from the group consisting of acrylate resins and methacrylate resins.
5. The sensor of claim 4 wherein said resin is a polymer of a hydroxy lower alkyl acrylate.
6. The sensor of claim 4 wherein said resin is a hydroxy lower alkyl methacrylate.
7. The sensor of claim 4 wherein said resin is a homopolymer of 2-hydroxyethyl methacrylate.
8. The sensor of claim 4 wherein said resin is a copolymer of 2-hydroxyethyl methacrylate.
9. The sensor of claim 3 wherein said hygroscopic resin is cross-linked with a cross-linking agent.
10. The sensor of claim 3 wherein at least one of said pair of electrodes has a lead of a metal selected from the group consisting of gold, platinum, palladium, rhodium and alloys thereof.
11. The sensor of claim 3 wherein said base plate is a window glass of an automobile, and the humidity-sensitive sensor is on the inside surface of said window glass.

* * * * *